United States Patent
Liang

(10) Patent No.: US 9,826,899 B2
(45) Date of Patent: Nov. 28, 2017

(54) METHODS AND DEVICES FOR REFRACTIVE CORRECTION OF EYES

(71) Applicant: PERFECT VISION TECHNOLOGY (HK) LTD., Tsuen Wan (HK)

(72) Inventor: Junzhong Liang, Fremont, CA (US)

(73) Assignee: PERFECT VISION TECHNOLOGY (HK) LTD., Tsuen Wan, NT (HK)

( * ) Notice: Subject to any disclaimer, the term of this patent is extended or adjusted under 35 U.S.C. 154(b) by 0 days.

(21) Appl. No.: 15/142,544

(22) Filed: Apr. 29, 2016

(65) Prior Publication Data
US 2016/0242641 A1    Aug. 25, 2016

Related U.S. Application Data

(60) Division of application No. 14/465,755, filed on Aug. 21, 2014, now Pat. No. 9,345,399, which is a division
(Continued)

(51) Int. Cl.
*A61B 3/10* (2006.01)
*A61B 3/103* (2006.01)
(Continued)

(52) U.S. Cl.
CPC ............ *A61B 3/103* (2013.01); *A61B 3/0025* (2013.01); *A61B 3/0285* (2013.01);
(Continued)

(58) Field of Classification Search
CPC ......... A61B 3/103; A61B 3/1015; A61B 3/14; A61B 3/12; A61B 3/04; A61B 3/02
(Continued)

(56) References Cited

U.S. PATENT DOCUMENTS

| 2,021,812 A | 11/1935 | Scott |
| 3,431,688 A | 3/1969 | Rudd et al. |

(Continued)

FOREIGN PATENT DOCUMENTS

| CN | 2031935 | 2/1989 |
| CN | 1781443 A | 6/2006 |

(Continued)

OTHER PUBLICATIONS

Extended European Search Report dated Jul. 5, 2016 for European Patent Application No. 13859414.8.
(Continued)

*Primary Examiner* — James Greece
(74) *Attorney, Agent, or Firm* — The Mueller Law Office, P.C.

(57) ABSTRACT

Methods and devices are provided to obtain refractive correction with superior visual acuity (e.g., 20/10) by achieving an astigmatism-free customized refractive correction. The astigmatism-free customized refractive correction involves obtaining an objective and precise measurement of cylindrical power in a resolution between 0.01 D and 0.10 D in an eye using an objective aberrometer, reliably relating the cylindrical axis obtained from the objective aberrometer to that in a phoroptor, determining an optimized focus error of an eye through subjective refraction with a phoroptor, generating a customized refraction by combining the objective measured cylindrical power, the objective measured cylindrical axis, and the subjectively measured focus power, fabricating a custom lens with a tolerance finer than 0.09 D based on the generated customized refraction, and delivering an ophthalmic lens that can provide an astigmatism-free refractive correction for an eye.

6 Claims, 9 Drawing Sheets

Related U.S. Application Data of application No. 13/682,527, filed on Nov. 20, 2012, now Pat. No. 8,827,448, which is a division of application No. 13/116,262, filed on May 26, 2011, now Pat. No. 8,419,185, which is a continuation of application No. PCT/US2009/066148, filed on Nov. 30, 2009.

(60) Provisional application No. 61/200,494, filed on Dec. 1, 2008, provisional application No. 61/208,045, filed on Feb. 20, 2009.

(51) Int. Cl.
*G02C 7/02* (2006.01)
*A61B 3/00* (2006.01)
*A61B 3/028* (2006.01)
*G01M 11/02* (2006.01)

(52) U.S. Cl.
CPC ....... *A61B 3/1015* (2013.01); *G01M 11/0228* (2013.01); *G02C 7/02* (2013.01); *G02C 7/022* (2013.01); *G02C 7/027* (2013.01); *G02C 2202/22* (2013.01)

(58) Field of Classification Search
USPC ......... 351/205, 206, 222–223, 233–235, 246
See application file for complete search history.

(56) References Cited

U.S. PATENT DOCUMENTS

| | | | |
|---|---|---|---|
| 5,434,707 | A | 7/1995 | Dalzell et al. |
| 5,652,638 | A | 7/1997 | Roffman et al. |
| 5,777,719 | A | 7/1998 | Williams et al. |
| 6,108,634 | A | 8/2000 | Podnar et al. |
| 6,142,625 | A | 11/2000 | Sawano et al. |
| 8,167,429 | B1 | 5/2012 | Butler et al. |
| 8,419,185 | B2 | 4/2013 | Liang |
| 8,820,931 | B2 | 9/2014 | Walsh et al. |
| 8,827,448 | B2 | 9/2014 | Liang |
| 2001/0041884 | A1 | 11/2001 | Frey et al. |
| 2003/0151721 | A1 | 8/2003 | Lai et al. |
| 2004/0054358 | A1 | 3/2004 | Cox et al. |
| 2004/0169820 | A1* | 9/2004 | Dai et al. ............. 351/246 |
| 2004/0263786 | A1 | 12/2004 | Williams et al. |
| 2005/0104240 | A1 | 5/2005 | Jethmalani et al. |
| 2005/0174535 | A1 | 8/2005 | Lai et al. |
| 2005/0200809 | A1 | 9/2005 | Dreher et al. |
| 2005/0225724 | A1 | 10/2005 | Klyce et al. |
| 2006/0023163 | A1* | 2/2006 | Foster .................. 351/246 |
| 2006/0203198 | A1 | 9/2006 | Liang |
| 2006/0235369 | A1 | 10/2006 | Macrae et al. |
| 2006/0279699 | A1 | 12/2006 | Liang |
| 2007/0118428 | A1 | 5/2007 | Akiyama et al. |
| 2007/0159593 | A1 | 7/2007 | Hibino et al. |
| 2008/0018855 | A1 | 1/2008 | Larichev et al. |
| 2008/0143960 | A1 | 6/2008 | MacRae |
| 2008/0143963 | A1 | 6/2008 | Lindacher |
| 2009/0244480 | A1 | 10/2009 | De Gaudemaris et al. |
| 2009/0323020 | A1 | 12/2009 | Zhao et al. |
| 2010/0074477 | A1 | 3/2010 | Fujii et al. |
| 2010/0283963 | A1 | 11/2010 | Giraudet et al. |
| 2011/0228225 | A1 | 9/2011 | Liang |
| 2012/0057124 | A1 | 3/2012 | Spivey et al. |
| 2012/0271412 | A1 | 10/2012 | Feingold et al. |
| 2014/0368795 | A1 | 12/2014 | Liang |

FOREIGN PATENT DOCUMENTS

| | | |
|---|---|---|
| EP | 0857455 A2 | 8/1998 |
| GB | 1463107 A | 2/1977 |
| JP | S54131950 | 10/1979 |
| JP | S601604 A | 1/1985 |
| JP | H03229212 | 10/1991 |
| JP | H05332720 A | 12/1993 |
| JP | H06034920 | 2/1994 |
| JP | H08191794 A | 7/1996 |
| JP | H08215148 A | 8/1996 |
| JP | H0915541 A | 1/1997 |
| JP | H09015541 A | 1/1997 |
| JP | H10175149 A | 6/1998 |
| JP | H10216087 A | 8/1998 |
| JP | 11056779 A | 3/1999 |
| JP | H11113848 A | 4/1999 |
| JP | H11267100 A | 10/1999 |
| JP | H11295668 | 10/1999 |
| JP | 2001275966 A | 10/2001 |
| JP | 2002078679 A | 3/2002 |
| JP | 2002156611 | 5/2002 |
| JP | 2003504665 A | 2/2003 |
| JP | 2003140094 | 5/2003 |
| JP | 2003532476 A | 11/2003 |
| JP | 2004535881 A | 12/2004 |
| JP | 2005516717 A | 6/2005 |
| JP | 2005521473 A | 7/2005 |
| JP | 2005288176 A | 10/2005 |
| JP | 2006503738 A | 2/2006 |
| JP | 2006178245 A | 7/2006 |
| JP | 2006517135 A | 7/2006 |
| JP | 2007511796 | 5/2007 |
| JP | 2007514963 A | 6/2007 |
| JP | 2007240553 A | 9/2007 |
| JP | 2007531559 A | 11/2007 |
| JP | 2008508006 A | 3/2008 |
| JP | 2008113810 A | 5/2008 |
| JP | 2009521726 A | 6/2009 |
| JP | 2010513992 A | 4/2010 |
| JP | 2012510642 | 5/2012 |
| WO | 0108748 A1 | 3/2001 |
| WO | 03009746 A1 | 2/2003 |
| WO | 03068059 A2 | 8/2003 |
| WO | 2004039554 A2 | 5/2004 |
| WO | 2005040896 A1 | 5/2005 |
| WO | 2005050289 A1 | 6/2005 |
| WO | 2005050290 A1 | 6/2005 |
| WO | 2005079546 A2 | 9/2005 |
| WO | 2006010611 A1 | 2/2006 |
| WO | 2007075975 A2 | 7/2007 |
| WO | 2008049503 A2 | 5/2008 |
| WO | 2010065475 A | 6/2010 |
| WO | 2012054651 A2 | 4/2012 |

OTHER PUBLICATIONS

Office Action dated Sep. 23, 2016 for U.S. Appl. No. 14/646,734.
Extended European Search report dated May 13, 2014 for EP Aplication No. 09830937.0.
International Search Report and Written Opinion dated Nov. 28, 2013 for PCT Application No. PCT/IB2013/001051.
International Search Report and Written Opinion dated Apr. 9, 2014 for PCT Patent Application No. PCT/US2013/071763.
International Search Report and Written Opinion dated Jun. 25, 2010 for PCT Application No. PCT/US2009/066148.
Japanese Office Action dated Oct. 29, 2013 for JP Application No. 2011-538720.
Notice of Allowance dated Apr. 12, 2016 for U.S. Appl. No. 14/465,755.
Notice of Allowance dated Feb. 22, 2013 for U.S. Appl. No. 13/116,262.
Notice of Allowance dated Nov. 3, 2015 for U.S. Appl. No. 13/687,309.
Office Action dated Apr. 3, 2015 for U.S. Appl. No. 13/687,309.
Office Action dated Feb. 3, 2016 for U.S. Appl. No. 14/465,755.
Office action dated May 13, 2014 for Japanese Application No. 2011-538720.
Office Action dated Nov. 10, 2015 for Japanese patent application No. 2011-538720.
Office Action dated Sep. 30, 2015 for U.S. Appl. No. 14/465,755.
Pretrial ReExamination Report dated Nov. 28, 2014 for Japanese Patent Application No. 2011-538720.

(56) References Cited

OTHER PUBLICATIONS

Extended European Search Report dated May 3, 2016 for European Patent Application No. 13851854.7.
Office Action dated Jun. 21, 2016 for Japanese Patent Application No. 2011-538120.
Office Action dated Apr. 11, 2017 for Japanese Patent Application No. 2016-078887.
Office Action dated May 30, 2017 for Japanese Patent Application No. 2015-544550.
Notice of Allowance dated Jan. 12, 2017 for U.S. Appl. No. 14/646,734.
Office Action dated Feb. 7, 2017 for Japanese Patent Application No. 2016-093776.
Office Action dated Jan. 31, 2017 for Japanese Patent Application No. 2015-544550.
Office Action dated Aug. 8, 2017 for Japanese Patent Application No. 2015-545157.
Office Action dated Jul. 18, 2017 for Japanese Patent Application No. 2016-093776.
Office Action dated Oct. 17, 2017 for Japanese Patent Application No. 2016-078887.

\* cited by examiner

METHODS AND DEVICES FOR REFRACTIVE CORRECTION OF EYES

CROSS-REFERENCES TO RELATED APPLICATIONS

This application is a divisional of U.S. patent application Ser. No. 14/465,755 filed Aug. 21, 2014 and entitled "Methods And Devices For Refractive Correction Of Eyes"; which is a divisional of U.S. patent application Ser. No. 13/682,527 filed on Nov. 20, 2012 and entitled "Methods And Devices For Refractive Correction Of Eyes," and issued as U.S. Pat. No. 8,827,448; which is a divisional of U.S. patent application Ser. No. 13/116,262 filed on May 26, 2011 and entitled "Methods And Devices For Refractive Correction Of Eyes," and issued as U.S. Pat. No. 8,419,185; all of which are hereby incorporated by reference. U.S. patent application Ser. No. 13/116,262 is a continuation of International Patent Application No. PCT/US2009/066148, filed Nov. 30, 2009, which claims priority to provisional U.S. patent application No. 61/200,494 titled "Methods and processes for refractive correction of an eye" by Liang, filed Dec. 1, 2008, and provisional U.S. patent application No. 61/208,045 titled "Methods and devices for high-definition refractive correction of human eyes" by Liang, filed on Feb. 20, 2009, which are incorporated herein by reference.

FIELD OF THE INVENTION

The invention relates generally to refractive correction of eyes, and more specifically to the correction of myopia, hyperopia, and presbyopia.

BACKGROUND OF THE INVENTION

Refractive corrections for human eyes can be characterized into two general categories. The first category is the conventional method of vision correction which corrects for and the eye's focus error and cylindrical error as measured using a manifest refraction. The second category is wavefront-guide vision correction which provides correction for all aberrations in an eye, including focus error, cylindrical error, spherical aberration, coma, and others, measured using an objective wavefront sensor.

The conventional method of vision correction is conceptually limited to a correction of just focus error and cylindrical error. In addition, it is also constrained by the subjective nature of how the manifest refraction determines the eye's refractive errors, particularly the eye's cylindrical error. Cylindrical error is also known as astigmatism, and it causes particular problems because it includes both a cylindrical power and a cylindrical axis.

There are at least five limiting factors associated with a manifest refraction. First, manifest refraction is limited by available lenses in a phoroptor, because a manifest refraction relies on applying corrective lenses and testing vision of the eye subjectively. Focus error is usually limited to a resolution of 0.125 Diopters (D) while the cylindrical error is limited to a resolution of 0.25 D. Second, subjective determination of cylindrical axis can be problematic because a slight variation of cylindrical axis—within only a few degrees—can cause a significant performance difference for a cylindrical correction of more than 2 D. Third, human errors by either the patient or a practitioner—such as an optometrist or optician—cannot be excluded because a manifest refraction involves the subjective responses of a patient to a plurality of refractive corrections, as well as the practitioner's analysis of those subjective responses. Fourth, a manifest refraction is fundamentally a partial empirical refractive solution, because a practitioner conducting the manifest refraction determines an end point for a refractive correction in a time-consuming process. Finally, manifest refraction can also be a time consuming process because it relies on human control of vision optimization with as many as three independent variables which include a focus error, a cylindrical power, and a cylindrical axis.

The drawbacks associated with using a manifest refraction compound with the high tolerance of current lens manufacturing techniques and lead to widespread erroneous vision correction. The inaccuracy of the conventional vision correction method using a manifest refraction leads to a situation where there may be significant differences in a refractive prescription of the same eye by different practitioners, as well as in a coarse resolution of cylindrical power—as large as 0.25 D—universally prescribed for conventional vision correction. Consequently, available ophthalmic lenses in today's ophthalmic industry are also limited to lenses in 0.25 D resolution. Correcting an eye's astigmatism using conventional vision correction is further complicated by the high tolerance in fabricating conventional spectacle lenses. As illustrated in the British standard for tolerances on optical properties of mounted spectacle lenses, BS 2738-1:1998, the tolerance of cylindrical power ranges from ±0.09 D for low power lenses to ±0.37 D for high power lenses. It is safe to say that uncorrected astigmatism by today's ophthalmic lenses is as large as 0.37 D due to the combined errors in the manifest refraction and the tolerances associated with making ophthalmic lenses.

Advanced wavefront sensing that provides reliable measurement of all aberrations in an eye with an objective wavefront sensor is described in U.S. Pat. No. 5,777,719 by Williams and Liang. In theory, wavefront-guide vision correction could provide perfect aberration-free refractive correction for every eye, because all aberrations can be measured objectively. In reality, however, wavefront-guide vision correction also has its challenges. First, manufacturing a lens with precise control of all aberrations across the lens can be complicated and expensive, because it is impossible to use the conventional processes for manufacturing spherical lenses, toric lenses, and aspheric lenses. Second, wavefront corrections require precise wavefront alignment between a lens and an eye at all times. The combination of these issues in lens manufacturing and in wavefront sensing makes it very difficult to achieve wavefront-guided corrections for conventional lenses such as spectacles, contact lenses, and implantable lenses.

Consequently, although many configurations and methods for vision correction are known in the art, all of them suffer from one or more disadvantages. Thus, there is a need to provide improved methods and devices to achieve practical uncompromised vision correction.

SUMMARY OF THE INVENTION

In one aspect of the invention, a method for determining a refractive correction of an eye is provided. In a first step, an objective measurement of a wave aberration of the eye's obtained without the use of a patient's responses. In a next step, a measured cylindrical power and a cylindrical axis are determined from the objective measurement. The cylindrical power determined has a resolution finer than 0.25 D, thus less than 0.25 D. In a third step, a focus power of the eye is determined through subjective refraction, which involves a patient's subjective responses to a plurality of refractive corrections. In a fourth step, a customized prescription for an ophthalmic lens or a refractive procedure is obtained by combining the cylindrical power and cylindrical axis from the objective measurement, and the focus power from said subjective measurement. The customized prescription has a cylindrical power with a resolution finer than 0.25 D.

In another aspect of the invention, a business for delivering customized ophthalmic lenses for refractive correction for human eyes is provided. In a first step, a cylindrical power of an eye in a resolution finer than 0.25 D and a cylindrical axis are obtained through a high-precision objective refraction without patient response. In a second step, a spherical focus power of said eye is determined through a subjective refraction wherein the subjective refraction involves measuring a vision performance of the eye based on subjective responses to a plurality of refractive corrections. In a third step, a customized refractive prescription for an ophthalmic lens or for a refractive procedure is generated by combining the cylindrical power, cylindrical axis, and spherical focus power, wherein the cylindrical power has a resolution finer than 0.25 D. In a fourth step, the customized refractive prescription is submitted to a lens vendor for fabricating a customized ophthalmic lens with a precise control of the cylinder power in a resolution finer than 0.25 D. In a fifth step, the customized ophthalmic lens is received and inspected with an objective lensometer. In a sixth step, the customized ophthalmic lens is delivered to a customer only if the measured cylindrical power of the customized ophthalmic lens and the cylindrical power in the lens prescription is less than 0.1 D.

In another aspect of the invention, an ophthalmic lens for a refractive correction of an eye is provided. The lens comprises a first toric surface and a second toric surface. Both of the toric surfaces have an associated cylindrical power. At least one of the first and second toric surfaces has a cylindrical power of less than or equal to 0.25 D.

In another aspect of the invention, a method of manufacture for producing an ophthalmic lens is provided. In a first step, a custom prescription for a toric lens with a spherical power, and a prescribed cylindrical power with a finer resolution than 0.25 D is received. In a second step, a customized toric lens is fabricated using either a lens molding or by surfacing a semi-finished blank. In a third step, the surface parameters of the customized toric lens are inspected. In a next step, one of the lens surfaces is reworked if the inspected surface is out of a desired specification. In a next step, the refractive power of the customized toric lens is measured with a lensometer. Finally, the customized toric lens is delivered if the measured cylindrical power of the customized toric lens matches the prescribed cylindrical power within a tolerance of between 0.01 D and 0.08 D In another aspect of the invention, a method of manufacture for producing an ophthalmic lens is provided. In a first step, a custom prescription of an ophthalmic lens with a spherical power, and a cylindrical power with a finer resolution than 0.25 D Is received. In a second step, a semi-finished blank is selected from a lens manufacturer. In a third step, the semi-finished blank is placed in a lens surfacing system. In a fourth step, the surface of the semi-finished blank is surfaced based on said custom prescription and a set of know refractive properties of the semi-finished blank to create a fabricated lens. In a fifth step, the refractive power of said fabricated lens is measured with a lensometer to determine the refractive error between said refractive power and said custom prescription. In a final step, the surface is reworked based on the determined refractive error until a measured cylindrical power of the fabricated lens and the cylindrical power of the prescription are within a tolerance of between 0.01 D and 0.08 D.

In another aspect of the invention, a phoroptor for measuring refractive errors of an eye is provided. A wavefront sensing module provides an objective measurement of the eye's aberrations. The objective measurement includes a focus error, a cylindrical axis, and a cylindrical power in a resolution finer than 0.25 D. An output module displays the objective measurement. A mechanical mechanism is capable of moving the wavefront sensing module to a first position for measuring the objective measurement and another position away from an optical axis of said eye for other measurements of said eye. A phoroptor module performs subjective refraction of the eye using a plurality of spherical lenses and cylindrical lenses. A mechanism in said phoroptor module is used for dialing in the cylindrical power and the cylindrical axis obtained from the output module.

In another aspect of the invention, a method of manifest refraction is provided. In a first step, an objective estimation of said eye's focus error, cylindrical power, and cylindrical axis using an objective refractor is obtained. The obtained focus power has a resolution of 0.25 D and the cylindrical power has a resolution finer than 0.25 D. In a second step, orientation information of the eye in reference to the objective refractor is stored. In a third step, the orientation of a phoroptor is aligned with the eye based on the stored orientation information. In a fourth step, the cylindrical axis and cylindrical power are dialed-in. In a fifth step, a revised focus power is determined subjectively in order to offer an optimized correction of the eye for far vision. In a sixth step, a refractive prescription for an ophthalmic lens or a refractive procedure is generated by combining the cylindrical power, cylindrical axis, and focus power.

Various objects, features, aspects and advantages of the present invention will become more apparent from the following detailed description of preferred embodiments of the invention.

DETAILED DESCRIPTION OF THE PREFERRED EMBODIMENTS

Reference now will be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the spirit and scope thereof. For instance, features illustrated or described as part of one embodiment may be used with another embodiment to yield a still further embodiment. Thus, it is intended that the present subject matter covers such modifications and variations as come within the scope of the appended claims and their equivalents.

Improved Methods for Determining a Refractive Correction of an Eye

Figure 1:
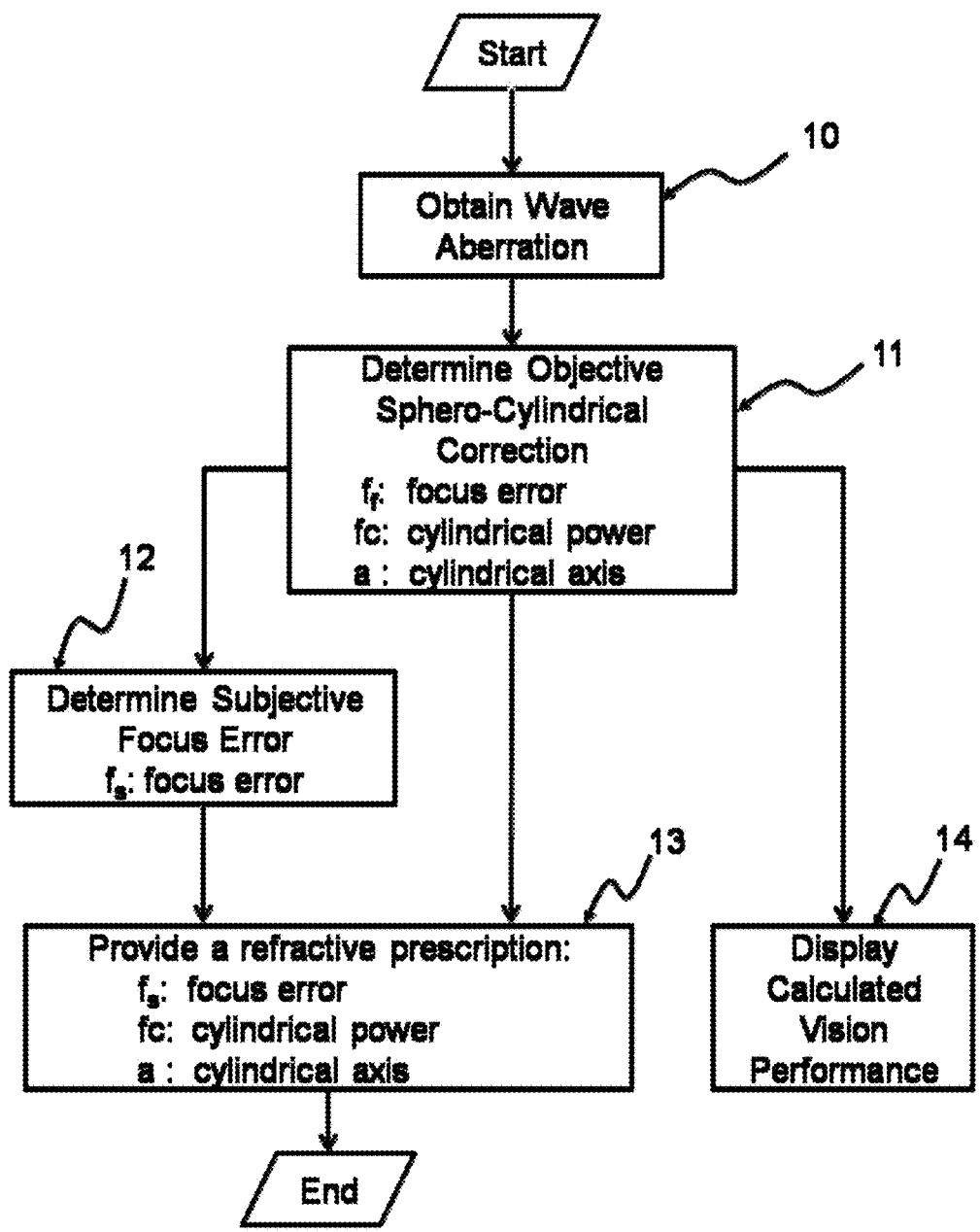
FIG. 1 shows a flow chart for a method for determining a refractive correction of an eye that is in accordance with the present invention.

FIG. 1 shows a flow chart for an improved method for determining a refractive correction of an eye based on an objective measurement of the eye's wave aberration and a subjective measurement of the eye's focus error in accordance with the present invention. This improved method will enable the production of an optimized astigmatism-free refractive correction so that a majority of normal human eyes can achieve visual acuity of 20/10 instead of conventional 20/20.

First, in step 10, an objective measurement of all the aberrations in an eye is obtained, wherein all aberrations are expressed in a wave aberration W(x,y). Second, in step 11, an objective sphero-cylindrical correction is determined from the obtained wave aberration by optimizing vision of the eye through removal of measured focus errors and cylindrical errors. The objective sphero-cylindrical correction comprises a focus error, a cylindrical power, and a cylindrical axis. Third, in step 12, a focus error of the eye is obtained through a subjective refraction, wherein the subjective refraction involves measuring vision performance of an eye based on subjective responses to a plurality of refractive corrections. Finally, in step 13, a refractive prescription for an ophthalmic lens or refractive procedure is generated by combining the objectively determined cylindrical power, the objectively determined cylindrical axis, and the subjectively determined focus error.

The method described has many advantages in comparison to conventional vision correction. First, cylindrical error in an eye as little as 0.025 D can be precisely determined just like other high-order aberrations such as spherical aberration and coma in an eye, because the refraction process does not depend on the limited cylindrical lenses in a phoroptor, subjective feedback about the fine difference between different cylindrical corrections by the tested subjects, and subjective optimization strategies used by the practitioners. Second, the cylindrical axis can be precisely determined and a tolerance for an error in cylindrical axis can be determined from the calculated image quality of an eye. Finally, vision optimization is no longer limited to a specific situation in a manifest refraction. Instead, virtual optimization can be applied to take account of different conditions of vision at different pupil sizes through the use of vision simulation of outdoor vision, indoor vision, and night vision.

In contrast to the objective wavefront refraction using a wavefront aberrometer as described in U.S. Pat. No. 5,777,719 by Williams and Liang, the method described also addresses the issue of measuring focus error in the eye using an objective refraction. Objective wavefront sensors like a wavefront aberrometer can measure focus error accurately, but cannot guarantee that the measured focus error is the best for far vision of an eye for two reasons. First, human eyes are known to change focus power by the crystalline lens at different viewing distances, which is also called accommodation. An objective wavefront sensor can only measure the focus error of an eye at one particular accommodation state. Second, objective wavefront sensors like an objective aberrometer only measure focus error of an eye at one particular wavelength of light, which is often in the infrared spectrum to assure the patient remains comfortable during the objective refraction. Chromatic aberration for perception must be taken into account for determining the best focus for an eye for the far accommodation point. Therefore, the focus error obtained from an objective refractor could be the true focus error for the far accommodation point within ±0.125 D for only about 20% of measured eyes.

About 40% of eyes will be under-corrected based on the focus error derived from an objective refractor, which will lead to a visual acuity below 20/20. At the same time, another 40% will be over-corrected based on the focus error obtained from an objective refractor, which leads to hyperopic vision after the refractive correction. The improved method for determining a refractive correction discussed here in accordance with the present invention uses a subjective approach to revise the focus error from the objective refractor, and thus takes into account both accommodation and chromatic aberration for an optimized refraction of the eye's far accommodation point.

The described improved method for determining a refractive correction can further include a preview of vision correction, as in step 14, even before an ophthalmic lens is made. Prediction of vision may include convolved retinal images of acuity charts, calculated modulation transfer functions, calculated point-spread functions, and simulation of nighttime symptoms. The calculated vision performance can be shown to a patient as well as a practitioner for accepting or selecting a specific refractive correction.

Figure 2:
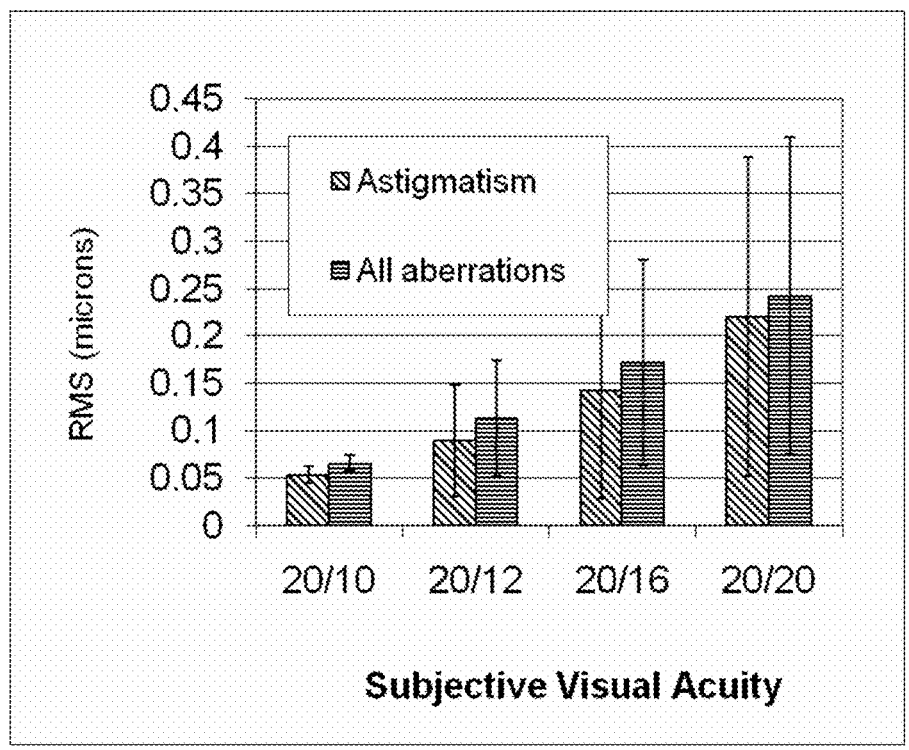
FIG. 2 shows aberrations in emmetropic eyes having subjective visual acuity better than 20/20 without any refractive correction.

The described improved method for determining a refractive correction enables an optimized astigmatism-free refraction for every eye. Perfect correction of an eye's cylindrical error can have significant impact on the visual acuity of a corrected eye. FIG. 2 shows the cylindrical error as well as the total aberration in more than 200 eyes with visual acuity better than 20/20 in a yet to be published clinical study. All the tested eyes are naturally emmetropic without any refractive correction. The cylindrical error and total aberrations in each eye are measured with an objective wavefront sensor and calculated based on the pupil size for each eye during the subjective measurement of visual acuity. The pupil size of acuity measurements ranges between 2.5 mm and 4.5 mm with an average pupil size of 3.7 mm. The error bars in FIG. 2 is one standard deviation for the measured population.

As can be seen in FIG. 2, the objectively measured cylindrical error and the subjectively measured acuity are correlated. In addition, it is clear that the cylindrical error is the dominate factor in determining subjective visual acuity.

Figure 3:
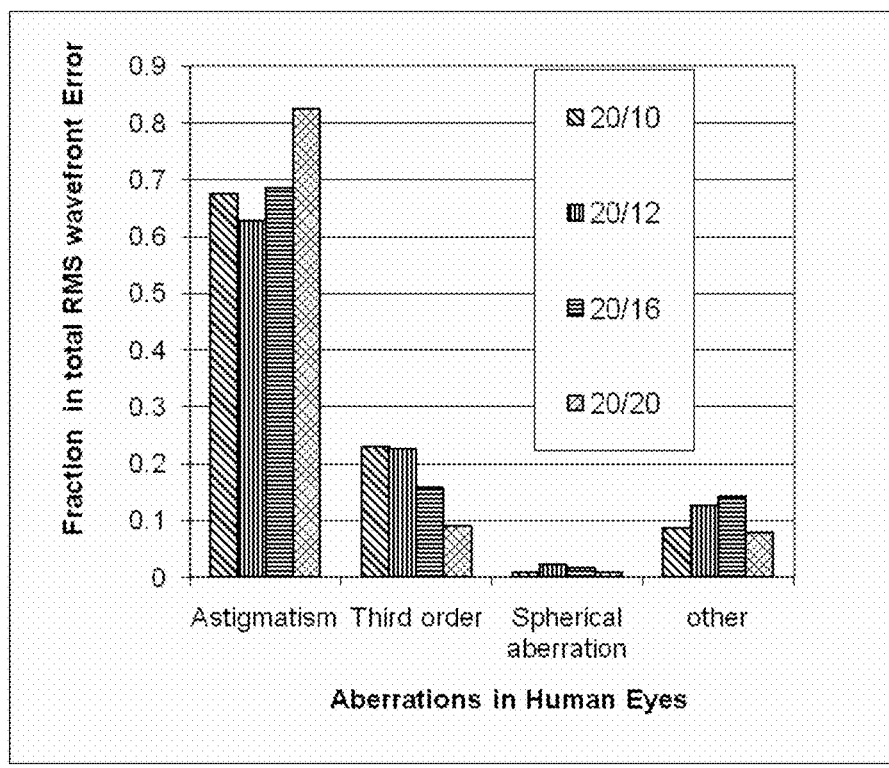
FIG. 3 shows fractions of different aberrations in the total aberration for emmetropic eyes having visual acuity better than 20/20 without any refractive correction.

FIG. 3 also highlights the importance of cylindrical error for visual acuity in naturally emmetropic eyes. FIG. 3 shows averaged fractions of different aberrations in the total aberrations for emmetropic eyes in four acuity groups in a yet to be published clinical study. It is seen that the cylindrical error accounts for 60% to 80% of all aberrations in emmetropic eyes in an acuity test. Coma has a much smaller contribution of 10% to 20%, while spherical aberration has negligible impact on visual acuity.

From the data in FIG. 2 and FIG. 3, it is not difficult to conclude that quality in correcting the cylindrical error in an eye has significant impact on subjective visual acuity. Visual acuity of 20/10 or 20/12 can usually be achieved just by a perfect correction of cylindrical error. Although important for vision at nighttime, additional correction of coma, spherical aberration, and other high-order aberrations has negligible impact on visual acuity for the majority of normal human eyes.

Perfect correction of an eye's cylindrical error requires precise measurements and specification of the cylindrical error in an eye. It is therefore necessary to specify cylindrical power much finer than the conventional resolution of 0.25 D, e.g. 0.025 D.

It is also important to record cylindrical axis in the objective measurement. One embodiment for recording the cylindrical axis is to record a digital picture of an eye while the objective measurement of cylindrical error is taken. The digital picture can later be used to assist the placement of an ophthalmic lens in an eye, or to verify proper orientation of an ophthalmic lens.

The described method for determining a refractive correction, when combined with innovations also described in the present application for advanced lens making, will enable an astigmatism free customized refractive correction that is superior in visual performance to the conventional method for vision correction based on conventional manifest refraction.

In one embodiment of the present invention, a method for obtaining an astigmatism-free customized refractive correction comprises the steps as follows. First, a wave aberration of an eye is obtaining objectively, wherein the wave aberration includes focus error, astigmatism, coma, and spherical aberration in the eye. Obtaining a wave aberration of an eye objectively can be achieved by measuring wave aberration of an eye using a device like an objective aberrometer as described in in U.S. Pat. No. 5,777,719 by Williams and Liang. Second, a cylindrical power and a cylindrical axis are determined from the objectively obtained wave aberration. The resolution for the cylindrical power must be finer than 0.25 D, e.g., 0.025 D. The specification for the determined cylindrical power has a resolution between 0.01 D to 0.1 D. Cylindrical axis must also be precisely determined. Third, a focus power of the eye is determined through subjective refraction. Subjective refraction can be achieved through the use of a phoroptor. Fourth, a refractive prescription for an ophthalmic lens or for a refractive procedure is generated by combining the objectively determined cylindrical power and cylindrical axis, and the subjectively determined focus power. Fifth, a customized ophthalmic lens is fabricated based on the generated high-precision refractive prescription with a high-precision cylindrical power. The cylindrical power has a resolution finer than 0.25 D, e.g., 0.025 D, with a tolerance between 0.01 D and 0.05 D. Additionally, the refractive correction can further include a spherical aberration that is determined from the wave aberration. Reducing spherical aberration in some eyes can improve night vision, particularly for those eyes with known nighttime symptoms such as glare and halo.

Figure 4:
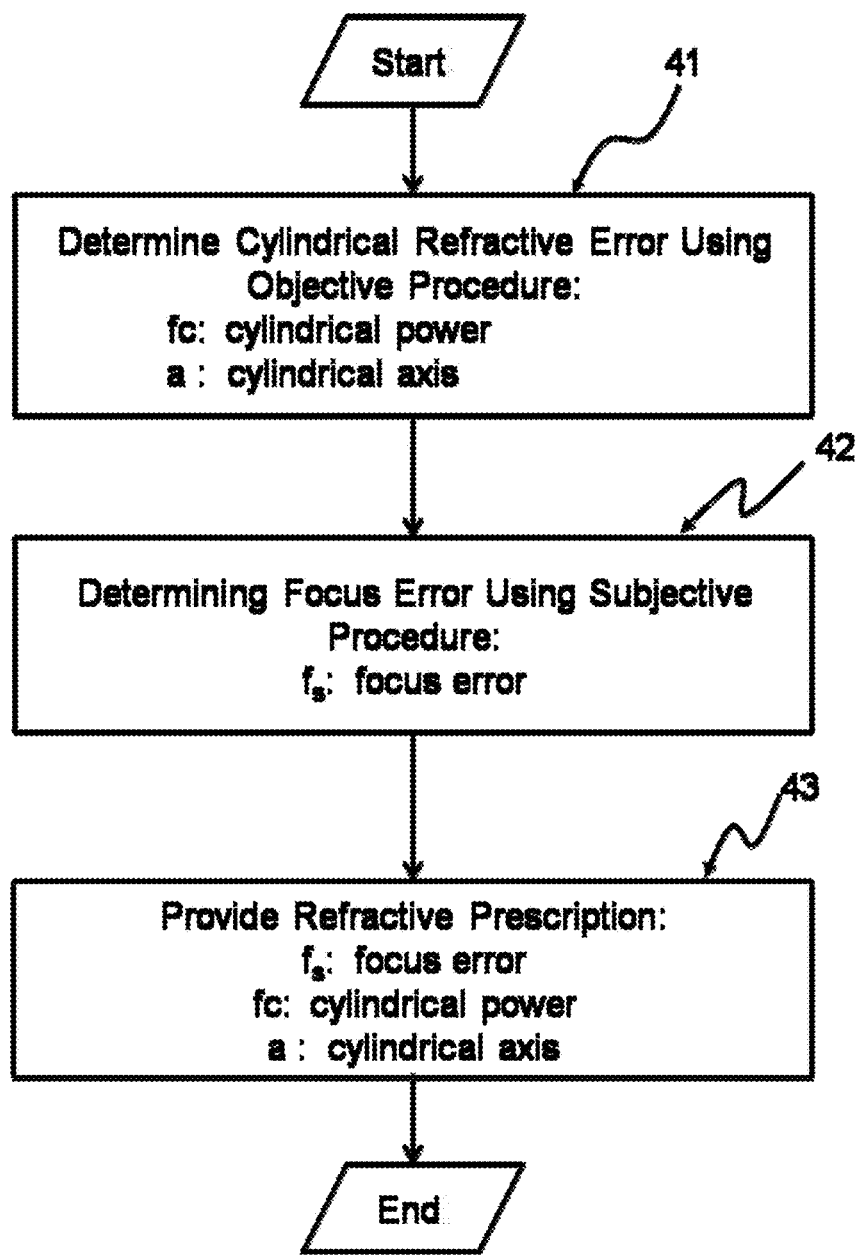
FIG. 4 shows a flow chart for a method for determining refractive correction of an eye in accordance with the present invention.

In another embodiment of the present invention, a simplified method for a perfect correction of eye's cylindrical error is shown in FIG. 4. This embodiment does not involve measuring high-order aberrations such as spherical aberration and coma. First, in step 41, a cylindrical error of an eye is determined using an objective procedure without any subjective responses. For improved accuracy in determining the cylindrical error, the objective procedure in step 41 might involve measuring refractive properties of an eye in a pupil size between 2.5 mm and 4 mm pupil, and taking an average measurement for a plurality of independent objective measurements. Second, in step 42, a focus error of the eye is determined through a subjective refraction measuring vision performance of an eye based on subjective responses to a plurality of refractive corrections. Third, in step 43, a refractive prescription for an ophthalmic lens or for a refractive procedure is generated by combining the determined cylindrical refractive error and the determined focus error, wherein the cylindrical error has a finer resolution less than the traditional 0.25 D, e.g., 0.025 D.

High-Precision Toric Lenses for Refractive Corrections

Due to the limitations in the conventional manifest refraction, ophthalmic lenses today are made with a cylindrical power resolution of 0.25 D. Corrections of astigmatism in human eyes using real spectacle lenses is further complicated because lenses are in reality made with a relative large tolerance of between ±0.09 D for low power lenses and up to ±0.37 D for high power lenses. Therefore, spectacle lenses for astigmatism-free customized refractive corrections must be made using more advanced technologies.

Spectacle lenses today are made using either: lens molding or lens machining using computer-controlled lathes. For the majority of spectacle lenses in a normal refraction range (spherical power between −6 D and +6 D), lenses are typically molded in batches, and stocked either in labs or in lens shops. Two lens molds are needed, and one mold has a base curve that is either spherical or aspheric in shape and the other mold has a toric shape if the spectacle lens has a cylindrical power. For lenses with a refractive power beyond the normal range, lenses are usually fabricated from semi-finished lens blanks that are molded in batches and stocked in factories. A semi-finished lens blanks contains a finished base surface in a spherical or aspheric curve and a top prescription surface that will be surfaced based on the lens prescription and optical power of the base surface. If the fabricated lens has a cylindrical power, the top surface will have a toric shape.

For both molded lenses and machined lenses with a cylindrical power, the finished lenses consists of a base curve that is spherical or aspheric in shape, and a prescription curve that is toric in shape for a prescription lens with a cylindrical power. The base curve is often set to one of 5 to 8 possible surface shapes, while the prescription surface must be capable of taking on the shape of one of several hundred curves in order for the combined lens to correct for different combination of spherical and cylindrical powers with the conventional resolution of 0.25 D.

For spectacle lenses with a fine cylinder resolution of 0.025 D instead of 0.25 D, manufactuers would need ten times more prescription curves if they continued to use the conventional lens shape with one toric surface. Although possible in theory, making custom lens for astigmatism-free correction using one toric surface would be prohibitively expensive because of the enormous number of molds that would be needed.

Figure 5:
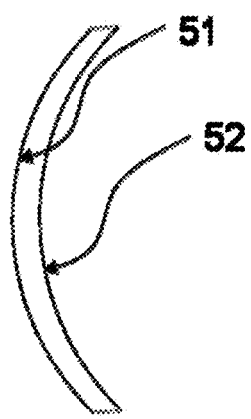
FIG. 5 shows an ophthalmic lens in accordance with the present invention.

FIG. 5 illustrates new spectacle lenses in accordance with the present invention for astigmatism-free customized refractive correction. In one embodiment of the present invention, the lens comprises a toric surface 51 that is a modified version of traditional base curves used in conventional lenses. A small amount of cylindrical power (<0.25 D) can be added to a traditional base curve for fine tuning cylindrical power at a resolution below 0.25 D. The other toric surface 52 can be the same as those used in making conventional toric lenses, which have cylindrical powers ranging from 0.00 D to 6.00 D with a resolution of 0.25 D. Both the base curve and the prescription curve can also have aspheric characteristics for reducing oblique astigmatism just like conventional toric lenses.

Two embodiments can be used for fine tuning cylindrical powers as fine as 0.025 D. One of the embodiments involves a fixed cylindrical power of 0.25 D or 0.125 D at the base curve, adjusting the angle between the two cylinder axes, and thereby achieving cylindrical power resolution as fine as 0.025 D. The other embodiment involves a plurality of cylindrical powers for each base curve (0.025 D, 0.05 D, 0.075 D, 0.10 D, 0.125 D, and 0.2 D), combining the cylindrical power from the base curve and the prescription curve, and thereby achieving fine cylindrical power as fine as 0.025 D. In the second embodiment, axes of the two toric surfaces can be made to coincide to achieve the designed cylindrical powers, or slightly different for further tuning of cylindrical powers.

For manufacturing lenses with two toric surfaces that both have cylindrical powers, it is important to control orientations of the two cylinder axes to achieve a desired cylindrical power. When a spectacle lens is molded with two toric molds, each mold can have a machine-readable mark. Two molds should be aligned on their cylinder axes before being put together to form a cavity for molding a lens. When a lens is machined for two toric surfaces, the semi-finished blanks can contain a machine readable mark to indicate the cylindrical axis of the finished surface. The cylindrical axis of the machined surface should be precisely controlled in reference to the axis of the pre-finished surface.

In another embodiment, the ophthalmic lens of in FIG. 5 can be further configured to induce spherical aberration at the central vision for the correction of spherical aberration in an eye. This can be achieved by shaping one of the two toric surfaces with an aspheric component around optical axis.

The ophthalmic lens of in FIG. 5 can further be configured to have aspheric shapes away from the optical axis for reduced off-axis Seidel aberrations. It can also be configured for a bi-focal lens or a progressive lens.

Controlling Cylindrical Power by Arranging Cylinder Axes of Toric Surfaces

Cylindrical powers in a fine resolution can be achieved by arranging the cylinder axes of two toric surfaces with coarse powers. In accordance with the present invention, the method requires two toric surfaces, where one of the two surfaces has a dominant cylindrical power in one direction $\Phi_{A1}$ while the other surface has a small biasing cylindrical power at a different orientation $\Phi_{A2}$. The angle between the two cylinder axes is measured by $\alpha$.

The combined cylindrical power can be expressed by an analytical expression:

$$\Phi_A = \text{SQRT}(\Phi_{A1}*\Phi_{A1}+\Phi_{A2}*\Phi_{A2}+2*\Phi_{A1}\Phi_{A2}*\text{COS}(2\alpha)) \quad (1)$$

where SQRT is the mathematic operator of square root. The combined cylindrical power $\Phi A$ is between $(\Phi_{A1}-\Phi_{A2})$ and $(\Phi_{A1}+\Phi_{A2})$, depending on the angle between the two cylinder axes. In one example, if the dominant cylindrical power $\Phi_{A1}$ has a cylindrical power of 1.0 D and the bias cylindrical power is 0.125 D, any cylindrical power in a fine resolution between 0.875 D and 1.125 D can obtained using these two base cylindrical powers. In another example, we can use a base bias cylindrical power of 0.25 D and 12 base dominant cylindrical powers of 0.25 D, 0.75 D, 1.25 D, 1.75 D, 2.25 D, 2.75 D, 3.25 D, 3.75 D, 4.25 D, 4.75 D, 5.25 D, 5.75 D, to achieve any cylindrical power between 0.00 D and 6.00 D with a resolution finer than 0.25 D.

There are three advantages associated with making a lens with a cylindrical power using two cylinder elements arranged at different cylinder axes. First, a high-resolution, adjustable cylindrical power can be achieved by arranging the relative orientation of the two cylinder axes. Controlling two cylinder axes within 2.5 degree is relatively easy in a manufacture process in comparison to a precise control of surface shape within 0.02 D. Second, making cylinder lenses in a fine resolution of cylindrical power is dramatically simplified and is low-cost because only a limited number of base molds are required. Third, a high-speed process can be achieved by fabricating all lenses with one bias power or just a few biasing cylindrical powers. High-definition lenses can then be custom manufactured just like a conventional lens with a limited number of cylindrical powers. One only needs to pay attention to the relative angle between the two cylinder axes.

It must be mentioned that arranging two cylindrical powers at various orientations will cause a variable focus offset to the base spherical power. The induced spherical power can be expressed as $$\Phi_S=0.5*(\Phi_{A1}+\Phi_{A2}-\Phi_A) \quad (2)$$

where $\Phi_{A1}$, $\Phi_{A2}$ and $\Phi_A$ are the dominate cylindrical power, the biasing cylindrical power and the combined cylindrical power, respectively. The total focus change depends on the angles between the two cylindrical axes, and can be as large as the biasing cylindrical power if the full range of angle between the two cylinder axes is 90 degrees. Because of the focus offset, this cylinder control method cannot be used for making conventional lenses with a resolution of 0.25 D.

When the bias cylindrical power is less than 0.25 D, the focus change in spectacle lenses can be addressed in two different ways. First, for eyes with significant accommodation range, the focus change in Eq (2) can be factored into the total spherical power. Second, for eyes with no or little accommodation, more than one bias power is needed to reduce the induced focus offset in Eq. (2). In this case, one may need five to ten bias powers and use a small angular range for fine tuning the combined cylindrical power.

In addition to making lenses with precise control of cylindrical power, the method of arranging two cylindrical powers described has three other applications. First, precise control of cylindrical power can be achieved even if the bias cylindrical power and the dominant cylinder are known to have manufacturing errors. A compensation angle can be calculated for eliminating the errors in the bias and dominant cylindrical powers. Second, one can use the principle described to build an improved phoroptor for preview of astigmatism-free custom vision corrections. Third, this method can also be used for making customized intra-ocular lenses.

Closed-Loop Methods for Making Customized High-Precision Toric Lenses

Customized spectacles for astigmatism-free refractive correction cannot be manufactured in today's labs using existing technologies because today's spectacle lenses are manufactured in a coarse resolution of 0.25 D and a rough tolerance between ±0.09 D to ±0.37 D as illustrated in British standard for tolerances on optical properties of mounted spectacle lenses (BS 2738-1:1998). Novel methods are required for making high-precision lenses for an astigmatism-free customized refractive correction.

A method for fabricating a customized toric lens for the high-definition refractive correction of a human eye in accordance with the present invention would utilize a closed-loop process. First, a manufacturer would receive a custom prescription of a toric lens with a spherical power, and a cylindrical power in a finer resolution than 0.25 D, e.g., 0.025 D. Second, desired surface profiles for a lens would be determined based on the obtained refractive prescription and the material used for making the ophthalmic lens. Third, a customized toric lens would be fabricated either through lens molding or by surfacing a semi-finished blank based on the determined surface profiles. Fourth, each fabricated custom lens would be measured with a lensometer. The lens would be delivered to a customer only if the measured cylindrical power of the manufactured lens and the cylindrical power in the custom prescription were within a custom tolerance level between 0.01 D and 0.08 D, e.g., 0.025 D. The lens would be reworked by surfacing at least one of the two surfaces if the difference between the measured cylindrical power of the manufactured lens and the cylindrical power in the custom prescription is not within a custom tolerance level.

In another embodiment of the present invention, the closed loop process for making a high-precision spectacle lens comprises the steps of: a) obtaining a prescription that comprises a spherical focus power, a cylindrical power, and an optional cylindrical axis and spherical aberration; b) determining desired surface profiles for a lens based on the obtained refractive prescription and the material used for making the ophthalmic lens; c) mounting a component in the form of an optical piece or a partially processed optical element into a manufacture system and altering at least one surface profile of the component according to the determined surface profiles; d) measuring refractive properties of the altered component using a lensometer; f) calculating residual errors of the manufactured lens from the obtained prescription data and the measured refractive data of the altered component; e) further changing at least one surface profile of the component based on the calculated residual errors until the residual errors of the manufactured lens are within a custom tolerance between 0.01 D and 0.08 D, e.g., 0.025 D.

Methods for Previewing an Astigmatism-Free Refractive Correction

Even though objective wavefront refractors provide precise measurements of cylindrical power and cylindrical axis of an eye, it is still preferred to preview the cylinder correction before a lens is made for the cylindrical correction.

A phoroptor is a device normally used in an optometry office for the subjective determination of a spherical focus power, a cylindrical power, and a cylindrical axis of an eye. Differences in cylindrical powers for a refractive correction are limited by a resolution of 0.25 D while differences in cylindrical axis are set by a resolution of about 5 degrees. Cylindrical axes in a phoroptor are never precisely related to an objective refraction in optometry practice. Therefore, conventional phoroptors in the prior art are not suited for high-definition refractive correction.

Figure 6:
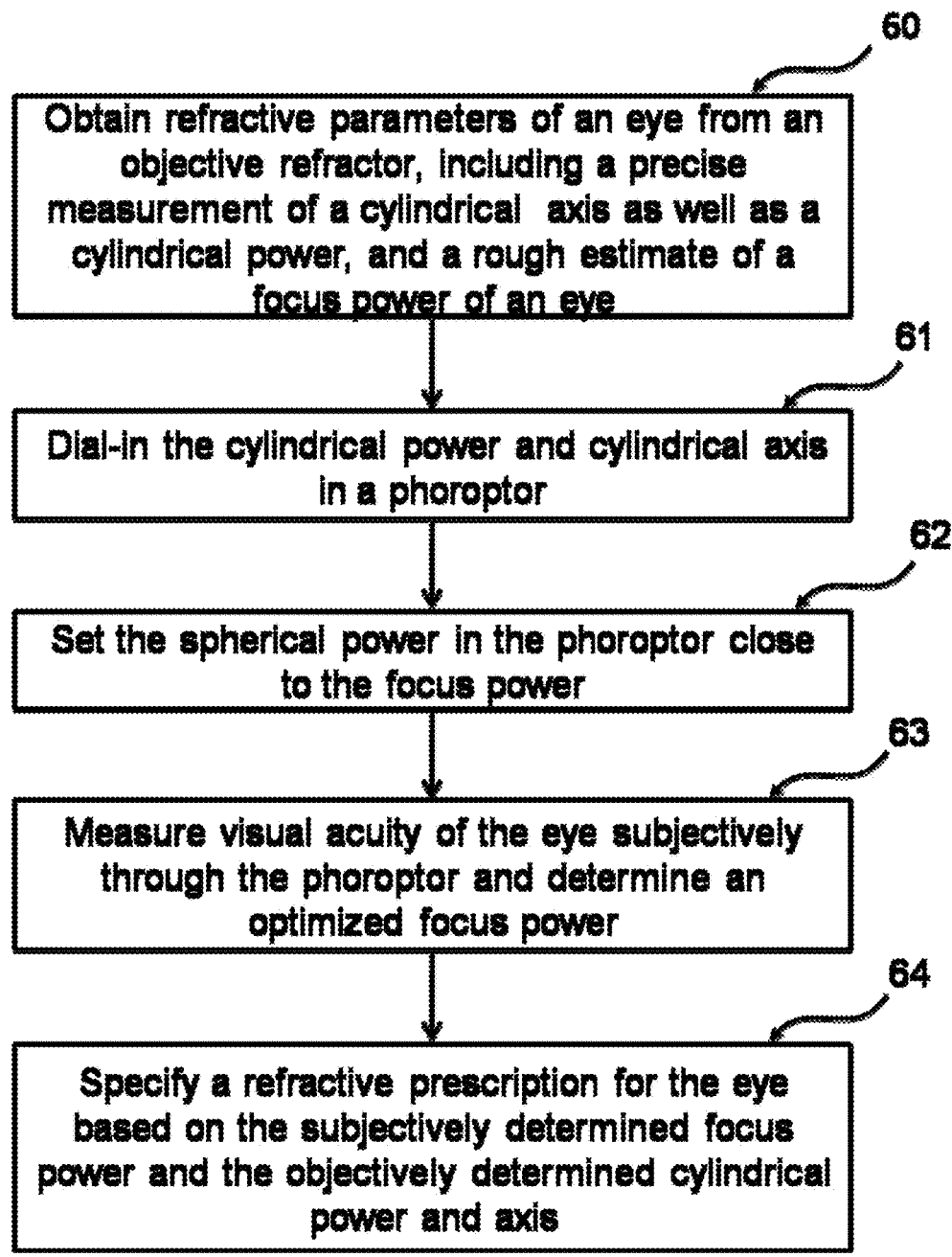
FIG. 6 shows a method for previewing a refractive correction of an eye in accordance with the present invention.

FIG. 6 shows a method for previewing an astigmatism-free refractive correction of an eye in accordance with the present invention. In one embodiment, the method for previewing an astigmatism-free refractive correction of an eye in accordance with the present invention comprises the steps of: a) obtaining a prescription of a refractive correction of an eye from an objective refractor 60, wherein the objective refractor measures wavefront slopes across the pupil of an eye, and precisely determines a cylindrical power (at resolution finer than 0.25 D), a cylindrical axis, an optional spherical aberration, and a rough estimate of a spherical focus power of an eye; b) dialing-in the determined cylindrical power and cylindrical axis in a phoroptor 61, wherein the cylinder parameters are controlled precisely with a resolution finer than 0.25 D; c) setting the spherical focus power to a plurality of values and measure visual acuity of an eye subjectively through phoroptor 62; d) determining an optimized focus power subjectively that sets the eye's accommodation at the far point 63; e) determine the best corrected acuity under preview and provide a refractive prescription 64 based on the subjectively determined focus power and the objectively determined cylindrical power and cylindrical axis.

Improved Phoroptors for Measuring Refractive Errors of an Eye

The method of previewing an astigmatism-free refractive correction in accordance with the method described above could be achieved using a phoroptor equipped with a wavefront aberrometer. In one embodiment, such an advanced phoroptor would comprise the following modules: a wavefront sensing module for providing an instant and objective measurement of an eye's aberrations; an output module for displaying the measured aberrations that include at least a focus error, a cylindrical axis and a cylindrical power in a resolution finer than 0.25 D, e.g., 0.025 D; a mechanical mechanism for moving the wavefront aberrometer to a position for measuring the eye's aberrations as well as for moving the wavefront aberrometer away from the optical axis of the eye for other measurements of the eye, a phoroptor module for performing subjective refraction of an eye using a plurality of spherical lenses and cylindrical lenses, wherein the phoroptor module may not correct high-order aberrations such as spherical aberration and coma; and a mechanism in the phoroptor module for dialing in a cylindrical power and cylindrical axis obtained from said output device of the wavefront aberrometer so that an astigmatism-free vision correction is achieved. The wavefront module would also measures all aberrations in the eye and provide image metrics derived from the measured aberration in the eye.

By design, conventional phoroptors in the prior art are not suited for astigmatism-free refractive corrections. An improved phoroptor must address the issues of relating the cylindrical axis of the phoroptor to the orientation of the eye in an objective refractor, and controlling cylindrical power in a resolution much finer than 0.25 D.

Figure 7:
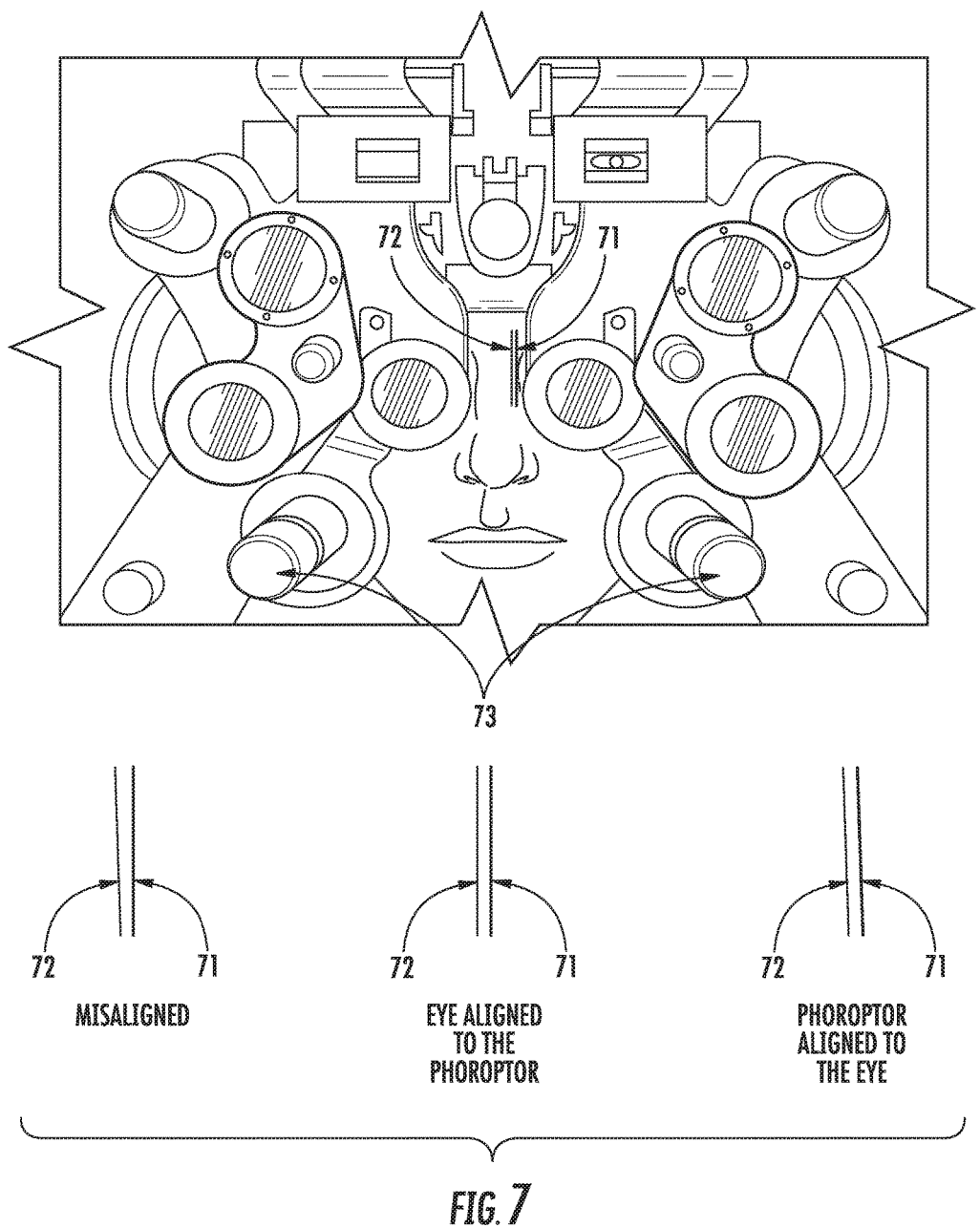
FIG. 7 shows a phoroptor for subjective refraction of an eye in accordance with the present invention.

FIG. 7 shows an improved phoroptor for subjective refraction of an eye in accordance with the present invention. A registration mark 72 is placed on face of a patient. An objective refraction of the eye can be obtained with its cylindrical axis relating to the alignment mark 72. When the same eye is placed behind a phoroptor, a light beam 71 from the phoroptor can be placed next to the registration mark for relating the cylindrical axis of the phoroptor to an orientation of the eye in another measurement.

Relating the cylindrical axis of a phoroptor to an orientation of an eye in an objective refractor may involve using the aid of a mechanical device, a light beam, a projected image, or an image device. Relating the cylindrical axis of a phoroptor to the cylindrical axis of an eye in an objective refractor may also involve comparing a fixed orientation such as an alignment mark 71 attached to a phoroptor to an orientation of an eye such as a registration mark 72 on the face of a patient or in an eye. Relating the cylindrical axis of a phoroptor to the cylindrical axis of an eye in an objective refractor may involve adjusting an orientation such as an alignment mark 71 attached to a phoroptor to match to an orientation of an eye specified by a registration mark 72 on the face of a patient or in an eye, and determining an angular offset from the adjustment to the alignment mark attached to the phoroptor.

The improved phoroptor can further include a digital control and display of its cylindrical axis instead of a manual control of the cylindrical axis 73. The digital control can be achieved using motorized control of the cylindrical axis.

The improved phoroptor can further include a mechanism for achieving cylinder correction continuously instead of every 0.25 D as in conventional phoroptors.

The improved phoroptor can further include a mechanism for achieving refractive correction of spherical aberrations in an eye using a plurality of phase plates or a plurality of lenses with aspheric surface profiles.

Figure 8:
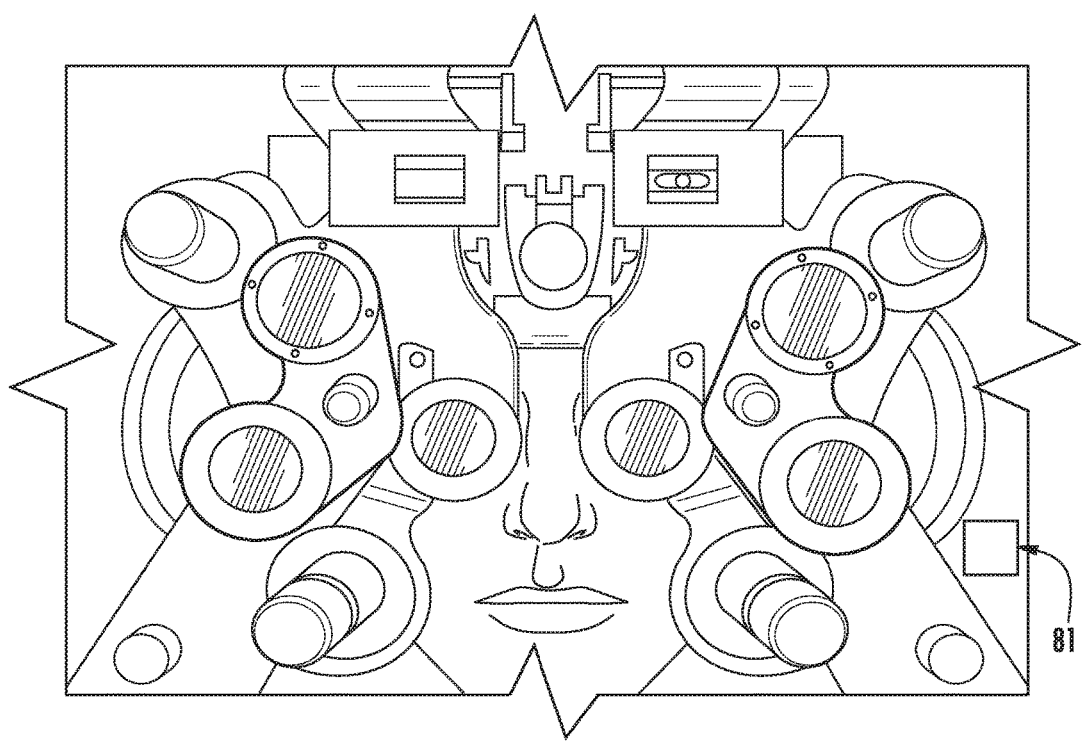
FIG. 8 shows another phoroptor for subjective refraction of an eye in accordance with the present invention.

In another embodiment, an improved phoroptor for subjective refraction of an eye includes a mechanism for entering a cylindrical power and a cylindrical axis manually or for importing refractive data from an objective refractor for improved efficiency and accuracy. Such a phoroptor is illustrated in FIG. 8 and comprises: a) a plurality of spherical lenses for the correction of defocus in an eye; b) a plurality of cylindrical lenses for the correction of astigmatism in an eye; c) a mechanism 81 for entering cylindrical power and cylindrical axis manually or for importing refractive data from an objective refractor.

Improved Objective Refractors for Refractive Correction of an Eye

A conventional wavefront aberrometer determines cylindrical error with high accuracy, but is not sufficient for astigmatism-free refractive correction in accordance with the present invention. This is because conventional wavefront aberrometers do not provide a reliable measurement of spherical focus power for setting an eye to its far accommodation point, and do not contain a mechanism to precisely link the cylindrical axis measured in an objective refractor to the cylindrical axis in a phoroptor for a subjective refraction or an ophthalmic lens.

Figure 9:
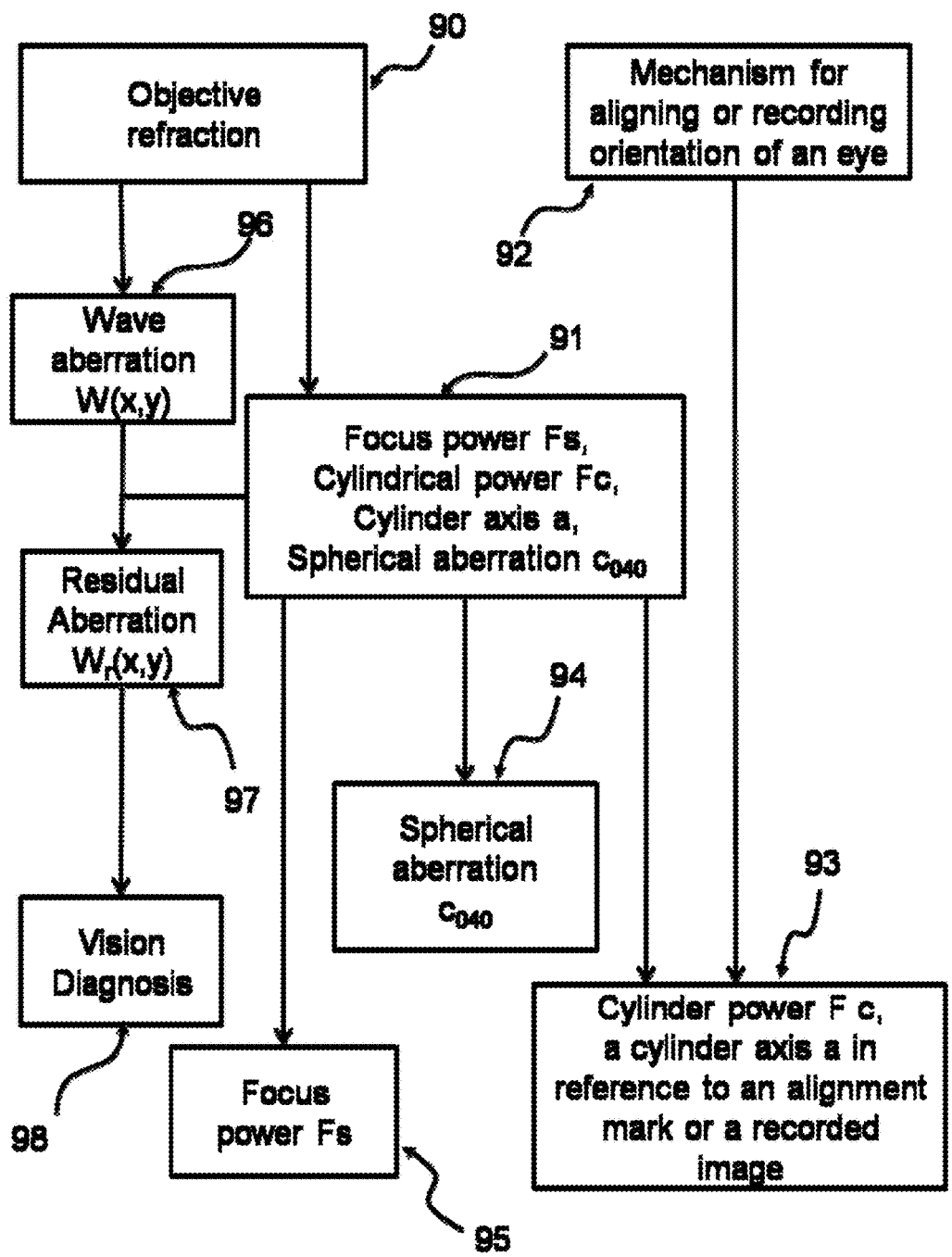
FIG. 9 shows a flow chart for an improved method for a manifest refraction in accordance with the present invention.

FIG. 9 shows an improved objective refractor system for a refractive correction. The system comprises an objective refraction device 90 for measuring refractive errors of an eye including at least a cylindrical power, a cylindrical axis, and a spherical focus error without any subjective response, and a mechanism for aligning orientation of an eye to a predetermined direction in the objective refractive device or for recording the facial orientation of an eye during an objective refraction 92.

In one embodiment, the objective refraction device 90 is an objective aberrometer that measures wavefront slopes across the pupil of an eye. The wavefront aberrometer will provide at least a spherical focus power, a cylindrical power, a cylindrical axis, and an optional spherical aberration of an eye to storage element 91. The focus power and optional spherical aberration will be available on output devices 95 and 94 respectively.

The mechanism for aligning or recording orientation of an eye 92 in one embodiment will allow changing relative orientation of an eye to a predetermined direction in the objective refraction device, and provide a visual aid for setting up the relative orientation between the refraction device and the eye under test. In combination with the data in storage element 91, the objective refractor system will be able to output a cylindrical power and cylindrical axis in reference to the alignment mark or recorded image in output device 93.

The mechanism for aligning or recording facial orientation of an eye 92 in one embodiment uses a digital camera to record at least a portion of a human face. The human face may include a man-made alignment mark, in the form of a frame for a spectacle lens without a refractive element.

In another embodiment, the objective refraction device can further provide total wave aberration of an eye 96, and vision diagnosis 98 based on the total wave aberration, data from a refractive correction, and a residual wave aberration 97, wherein the refractive correction includes a spherical focus power, a cylindrical power, a cylindrical axis, and an optional spherical aberration.

An Improved Manifest Refraction for Refractive Corrections

With the improved phoroptor and wavefront aberrometer according to the present inventions, we disclose an improved method of manifest refraction for astigmatism-free customized refractive correction. The method comprises of the following steps. First, an artificial registration mark is placed on a human face. Second, an objective estimation of the eye's focus error, cylindrical power, and cylindrical axis is obtained using an objective refractor. The focus power from the objective refraction has a resolution of 0.25 D and the cylindrical power has a resolution finer than 0.25 D, e.g. 0.025 D. The objective refractor is preferably a wavefront aberrometer. Third, orientation information of an eye in reference to the objective refractor is stored based on the artificial mark placed on the face. Fourth, before performing subjective refraction with a phoroptor, the tested eye in a phoroptor is aligned or checked based on the stored orientation information of an eye. Fourth, the optician dials in a cylindrical correction matching the obtained cylindrical power and cylindrical axis from the objective refractor. Fifth, a plurality of spherical corrections in addition to the dialed-in cylindrical correction is presented to the patient. A revised focus power is obtained as an improvement over the objectively measured focus error to offer an optimized correction of an eye for far vision. Sixth, a refractive prescription for an ophthalmic lens or a refractive procedure is generated by combining the objectively determined cylindrical refractive power and axis and the subjectively revised focus power.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the spirit and scope of the present invention, which is more particularly set forth in the appended claims. Furthermore, those skilled in the art will appreciate that the foregoing description is by way of example only, and is not intended to limit the invention.

What is claimed is:

1. A method of delivering customized ophthalmic lenses for human eyes for high-definition vision, comprising:
   determining a cylindrical power of an eye, as well as a cylindrical axis, wherein said cylindrical power and axis are determined from an objective measurement through an objective aberrometer without patient response;
   determining a spherical focus power of said eye through a subjective refraction, wherein said subjective refraction involves measuring a vision performance of said eye based on subjective responses to a plurality of refractive corrections;
   generating a customized refractive prescription for an ophthalmic lens or for a refractive procedure to produce an optimized astigmatism-free correction by combining said cylindrical power and said cylindrical axis from said objective measurement with said spherical focus power from said subjective refraction, wherein said cylindrical power has a resolution finer than 0.25 D;

submitting said customized refractive prescription to a lens vendor for fabricating a customized ophthalmic lens with a precise control of said cylinder power;

receiving and inspecting said customized ophthalmic lens with an objective lensometer; and delivering said customized ophthalmic lens to a customer only if a difference between a measured cylindrical power of said customized ophthalmic lens and said cylindrical power is less than 0.1 D.

2. The method in claim 1, wherein:

said objective measurement involves measuring refractive properties of said eye for a pupil size equal to or larger than 2.5 mm in diameter; and said cylindrical power is an average reading from a plurality of independent measurements.

3. The method in claim 1, wherein said subjective refraction is achieved with a phoroptor.

4. The method in claim 1, wherein the determined cylinder power in said objective measurement has a resolution between 0.01 to 0.1 D.

5. The method in claim 3, wherein said phoroptor comprises a plurality of spherical lenses, a plurality of cylindrical lenses, and an acuity chart for prediction of visions subjectively determining a focus error of said eye; and wherein said subjective refraction includes dialing said cylindrical power and said cylindrical axis in to said phoroptor according to said objective measurement.

6. The method in claim 1, wherein said objective aberrometer is a wavefront sensing module for measuring wave aberrations of said objective measurement.

\* \* \* \* \*